United States Patent [19]

Sitte et al.

[11] 4,306,425

[45] Dec. 22, 1981

[54] DEVICE FOR THE CRYO-SUBSTITUTION OF SMALL BIOLOGICAL OBJECTS FOR MICROSCOPIC RESEARCH, ESPECIALLY ELECTRON MICROSCOPIC INVESTIGATIONS

[75] Inventors: Hellmuth Sitte, Seefeld, Austria; Ludwig Edelmann, Homburg-Saar, Fed. Rep. of Germany

[73] Assignee: C. Reichert Optische Werke AG, Vienna, Austria

[21] Appl. No.: 185,035

[22] Filed: Sep. 8, 1980

[30] Foreign Application Priority Data

Nov. 3, 1979 [DE] Fed. Rep. of Germany ....... 2944464

[51] Int. Cl.³ ............................................. F25B 19/00
[52] U.S. Cl. ..................................... 62/514 R; 62/78; 165/30
[58] Field of Search .................... 62/45, 78, 514 R, 54, 62/125; 165/30

[56] References Cited

U.S. PATENT DOCUMENTS

| | | | |
|---|---|---|---|
| 3,538,714 | 11/1970 | Kling et al. | 62/54 |
| 4,218,892 | 8/1980 | Frosch et al. | 62/514 R |
| 4,232,453 | 11/1980 | Edelman | 62/514 R |

*Primary Examiner*—Ronald C. Capossela
*Attorney, Agent, or Firm*—Alan H. Spencer

[57] ABSTRACT

The invention concerns a device for the cryo-substitution of small biological objects for microscopic, especially electron microscopic investigations, with a metal receptacle for the reception of at least one object, which is mounted in a dewar flask containing a liquid cryogen and which can be regulated to a desired temperature by means of the cryogen and a regulatable heating device joined to the receptacle.

9 Claims, 2 Drawing Figures

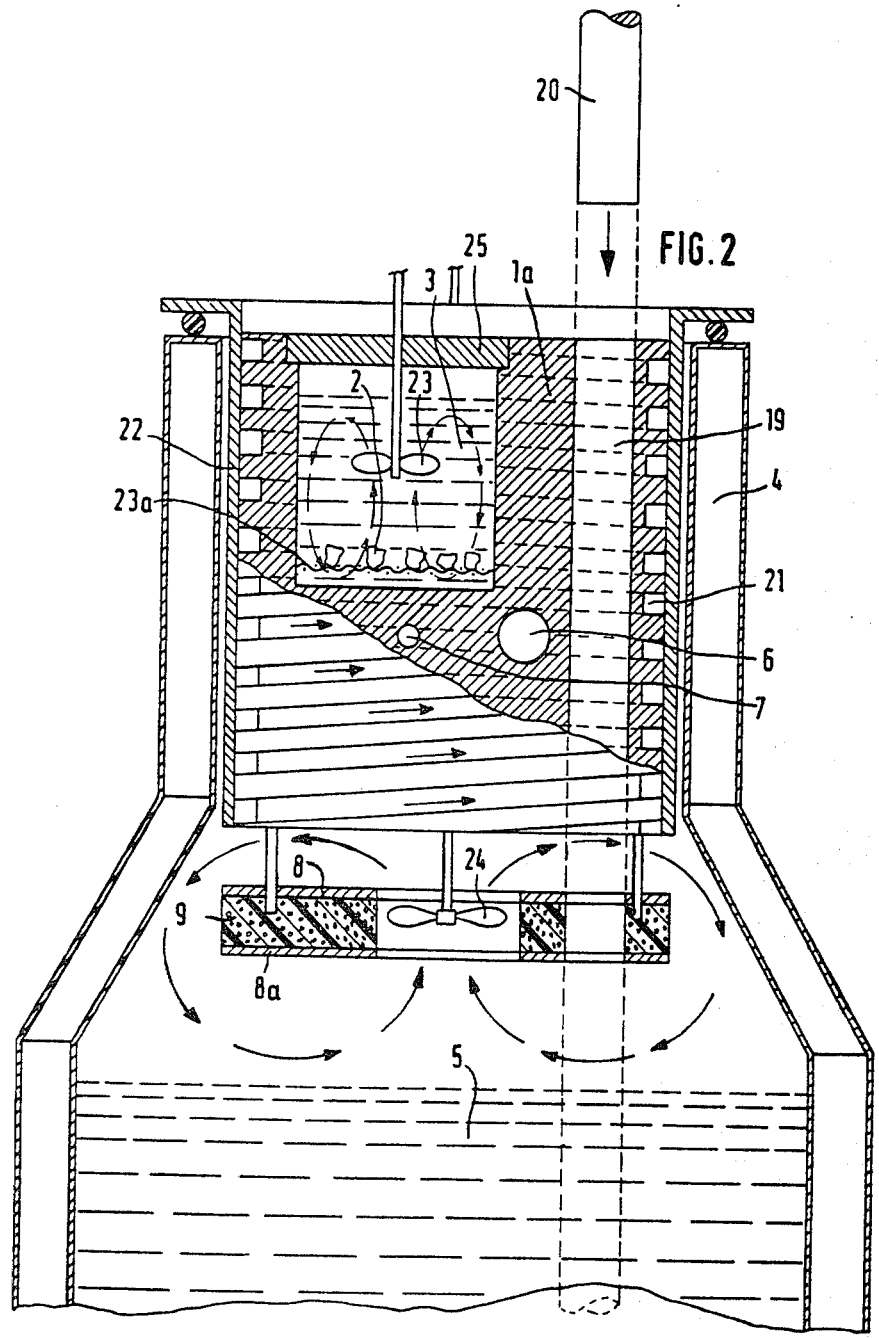

DEVICE FOR THE CRYO-SUBSTITUTION OF SMALL BIOLOGICAL OBJECTS FOR MICROSCOPIC RESEARCH, ESPECIALLY ELECTRON MICROSCOPIC INVESTIGATIONS

BACKGROUND OF THE INVENTION

For the purpose of quick stabilization, biological samples for microscopic, especially electron microscopic, investigations are, to an increasing extent, frozen extremely quickly (shock freezing). Subsequently, the water contained in the samples (often more than 90% by weight) is exchanged at low temperatures for suitable organic organic solvents, for example, water-free acetone or organic solutions, for example osmium-tetroxyde in water-free acetone. This exchange, at least in the critical initial phase, is completed at temperatures considerably under −30° C., since at temperatures over −30°, changes in the molecular structure of the objects can occur which reduce the value of the subsequent investigations. Therefore, to be on the safe side, the critical initial phase of the cryo-substitution often takes place in the temperature range between −80° and −120° C., which with the usual cold thermostats cannot be achieved at all, or only with great expenditure of equipment. The proportion in which this expenditure stands in relation to the small measurements and the limited number of such samples, does not justify the employment of expensive and bulky apparatus. Usually, for electron microscopy, for example, from one to ten tissue blocks with an individual volume of between 0.1 and 10 mm$^3$ are subjected to a cryo-substitution in one operation, which requires, according to the size of the objects and the substitution temperature, between three days and three weeks. During the stated time, the temperature must on no account exceed the respective limiting value to be determined for each object, since otherwise the sample can change in its molecular structure in such a way that reliable scientific statements about its structure in normal life conditions ("in vivo") can no longer be made.

For cryo-substitution up to now, only such laboratory devices have been used, which preferably consist of the samples being placed in closed containers in a freezing mixture of a familiar kind (for example, a dry ice mixture), which has the desired temperature. This procedure requires, however, continuous control as well as at least daily replacement of the freezing mixture. Insofar as the laboratory has at its disposal deep freezers for temperatures under −80°, this kind of system is used. Most morphology-oriented laboratories, however, do not have this kind of deep freezer. The acquisition of such a bulky and expensive system is mostly excluded, considering the space requirement, the installation load, as well as the investment costs.

The purpose of the invention under consideration is to make possible a cryo-substitution of small biological samples with an individual volume of under 10 mm$^3$ for a subsequent, especially electron microscopic investigation, by means of a device which is simple to make and to operate, and which makes possible the requisite low-temperature operation over several days or weeks with the necessary trustworthiness, without routine maintenance and with low routine operating costs.

According to the invention, this purpose is achieved in a device of the kind described above in that the receptacle is filled with a substitution medium, is mounted above the level of the cryogen in the dewar flask, and can be regulated to a temperature between −30° and −120° C. by a cold gas atmosphere circulating around it.

According to the invention there ensues, therefore, an exchange of the ice contained in the frozen biological samples for an organic fluid or solution, the substitution medium, that is poured into the receptacle with the objects. The temperature of between −+° and −120° C. required for the substitution process, in the framework of microscopic, especially electron microscopic, investigations, is thereby achieved in that the metal receptacle with the frozen biological samples is suspended in the substitution medium in the dewar flask containing liquid nitrogen or another suitable cryogen with a boiling point under −30° C. The metal receptacle thereby is not immersed in the cryogen, nor are the larger parts of its surfaces in direct, heat-conducting, metallic contact with the cryogen; rather, it is suspended in the dewar flask, above the level of the liquid cryogen in the dewar flask in such a way that it is not bathed or touched by the cryogen. However, it is mounted in such a way that it is constantly bathed by the continuously evaporating gas of the cryogen or respectively by the cold gas atmosphere, and thereby is cooled to the desired temperature.

SUMMARY OF THE INVENTION

The device according to the invention has, compared to the familiar laboratory devices for cryo-substitution, a number of substantial advantages: the design of the device is simple and entails only small manufacturing costs, since a familiar storage dewar can be used as the basic apparatus. The cryogen consumption during the cryo-substitution is scarecely more than the normal evaporation rate of the dewar flask, which, without a receptacle, is measured with the dewar flask sealed as usual. This evaporation rate, assuming the faultless condition of the dewar flask, lies, for the stocking of, e.g., liquid nitrogen, under a half liter per day. As a consequence of this low cryogen consumption, an unsupervised operation of the device over several days and weeks is readily possible. A 50 l dewar, given the aforementioned evaporation rate of under 0.5 l per day, for example, makes possible a substitution process with an overall duration of at least 100 days.

The receptacle contains a heating element as well as a temperature sensor, which make possible in a familiar manner the pre-selection and the thermostatic maintenance of a specific temperature value which has been determined to be optical for any given substitution process.

An advantageous elaboration of the invention provides for mounting between the underside of the receptacle and the level of the cryogen a radiation shield for reducing the heat radiation from the receptacle into the cryogen. In this way the evaporation rate of the cryogen is held to as low a value as possible.

The heat exchange between the receptacle and the gas atmosphere can be influenced in various ways. Thus, according to an effective elaboration of the invention, the surface of the receptacle can be adjusted and/or manipulated in its dimensions in order to achieve a specific heat exchange with the gas atmosphere. Alternately or additionally, at least a temporary gas circulation in the dewar flask can be provided for, in order to increase the heat exchange between the receptacle and the gas atmosphere.

According to an advantageous elaboration, moreover, a heat-conducting link can be produced in addition, with a predetermined thermal resistance between the receptacle and the liquid cryogen, in order to increase at least temporarily the heat exchange between the receptacle and the cryogen. This can be a so-called "cold finger," which is inserted when an especially low temperature within the stated temperature range has to be reached quickly. The resistance to heat conduction of this "cold finger" is determined by its cross section. One can also consider, however, making this cross section variable, in order to reach at any given time the heat flow necessary to reach and maintain the desired temperature.

A special advantage is that the regulatable heat device of the receptacle can be regulated by a semi or fully automatic control for the purpose of time-dependent control of the temperature curve. Thus one obtains an especially favorable substitution time with a low initial temperature, of, for example, −90° C., and higher temperature values in the further curve, for example, −60° C. after one week, and −30° C. after two weeks. It is expedient to program this temperature/time curve for a process computer, which controls the output of the heating element in the receptacle in a known manner with the use of a temperature sensor.

BRIEF DESCRIPTION OF THE DRAWINGS

Additional advantages and features of the invention are shown in the following description of preferred forms of construction with the help of the attached drawings, as well as in further subclaims. Shown in the drawings are:

THE PREFERRED EMBODIMENTS

Figure 1:
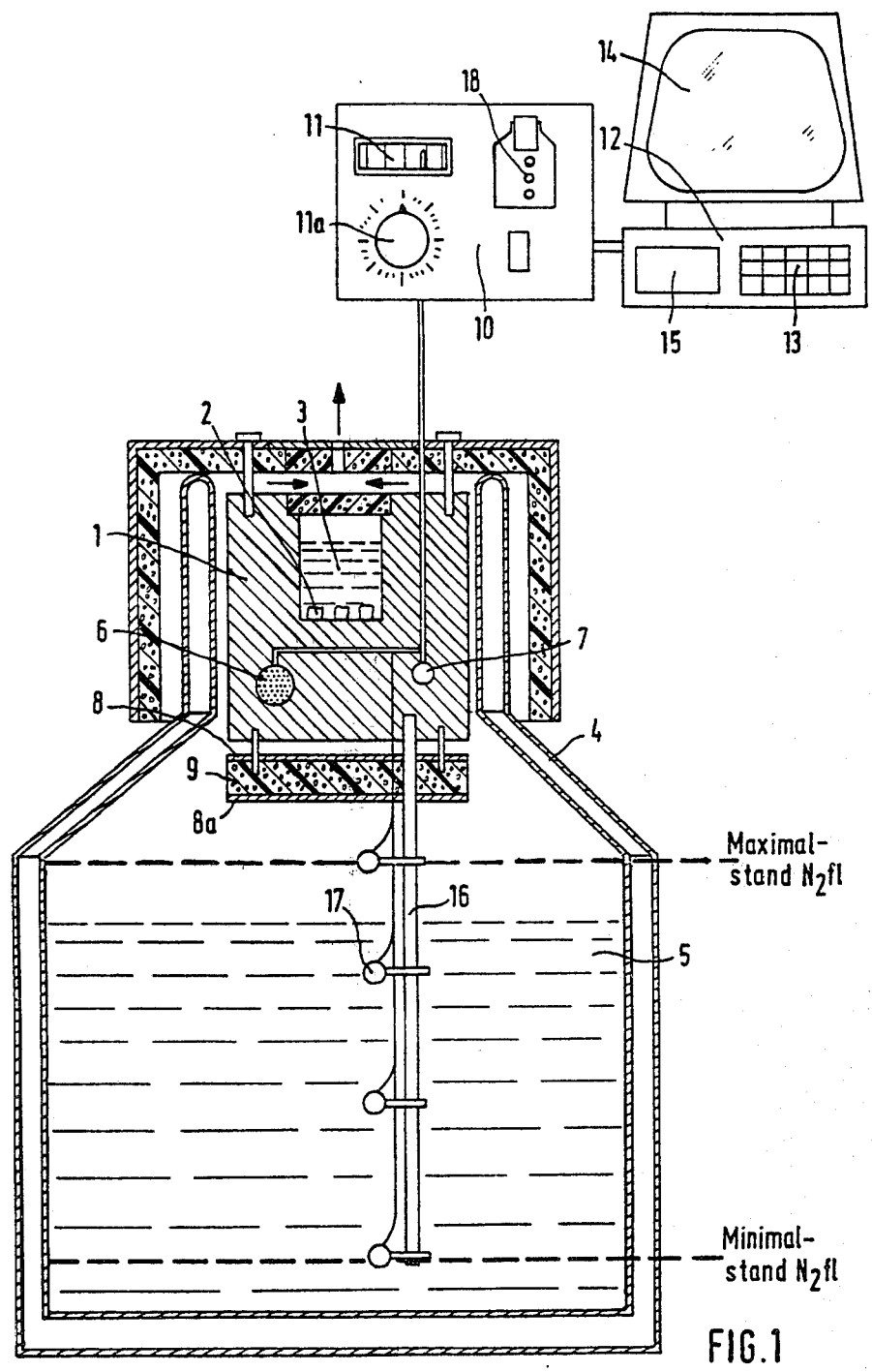
FIG. 1 is a schematic section through an early realization of a device for cryo-substitution in accord with the invention; and, FIG. 2, in enlarged scale, is a schematic section through a further realization with a metal receptacle modified with respect to the realization in FIG. 1.

The device according to the invention as described in FIG. 1 encompasses in essence a metal receptacle 1, closed by means of a lid, with a recess for the reception of the shock-frozen biological objects 2 and of the substitution medium 3, whereby the metal receptacle 1 is suspended in the neck of a dewar flask 4 in such a way that it is located above the surface of the liquid nitrogen 5 or of another suitable cryogen that has been poured in. The metal receptacle 1 is cooled by the nitrogen gas flowing around it (see the arrows). Its temperature can be changed by counter-heating with a heating cartridge 6, and also measured with a temperature sensor 7. Excessive cryogen losses due to the heat radiation of the heated metal receptacle can be prevented by means of a radiation shield 9 made, for example, of polystyrene foam and coated with highly polished aluminum foil 8 and 8a.

The heating cartridge 6 and the temperature sensor 7 can be connected in a known way to a controlling device 10, the circuitry of which permits the preselection, by means of a calibrated adjusting element 11a, of a temperature which can be read or read out 11, whereby a system-which will not be described further-guarantees the thermostatic maintenance of the pre-selected temperature.

A further elaboration of the device is possible, according to FIG. 1, by means of a connection to a process computer 12, the keyboard 13 of which makes possible the pre-selection of a temperature/time curve for the cryo-substitution as well as its presentation on a TV screen 14, or the input of prepared programs into a magnetic tape cassette 15. Finally, for the purpose of indicating the fill-level of the dewar flask at any given time, a row of measuring diodes 17 can be affixed to a rod 16, which indicate the fill-level by the light emitting diodes 18 on the control panel of the control device 10.

In the modified elaboration of the device as per FIG. 2, which in other respects in its overall arrangement, corresponds to the device according to FIG. 1, the metal receptacle 1a has a passage 19, through which, on the one hand, liquid nitrogen can be added to the dewar flask 4 without changing the position of the receptacle 1a; through which, on the other hand, a metal rod 20 can also be introduced, which, when it is completely inserted, dips into the liquid nitrogen and thereby produces a heat-conducting link between the metal receptacle 1a and the liquid nitrogen 5, which makes it possible to achieve lower temperatures, if necessary.

Reaching lower temperatures—by means, however, of a better exploitation of the heating capacity of the evaporating gaseous nitrogen—is also the aim of an enlargement of the surface of the metal receptacle 1a, which can be achieved either in simple form by means of vertical grooves, or, in the method represented, is realized by means of a helical groove 21, which substantially increases the contact length of the escaping gas, in conjunction with sleeve 22 fitted exactly to the external diameter of the receptacle 1a.

Finally, the overall duration of the substitution process can be substantially reduced by circulating the substitution medium 3 by means of a propeller 23, so that objects 2, lying, for example, on fine mesh 23a, are continually bathed and no concentration gradients, which slow the substitution, can build up on their surfaces.

The device described by FIGS. 1 and 2 can be developed, within the framework of the invention, in several variations and combinations. Thus, for example, it is possible to combine various individual solutions according to FIG. 1 and FIG. 2, to vary the surfaces characteristics for the purpose of increased heat exchange as well as to produce, inside the dewar flask 4, in a known manner—for example, by means of a propeller 24 mounted in a recess of the radiation shield 9—a gas convection which increases the cooling effect temporarily when needed, without establishing a metal contact (FIG. 2). This supplementary convection can furthermore be controlled electronically through the temperature sensor 7, according to the pre-selected temperature at any given time.

It is likewise immaterial what metal the receptacle 1 or 1a is made of, as well as with what surface coating it is provided, if necessary, for protection against corrosion, or for easier cleaning. Also, the way in which the electrical control apparatus 10 or the fill-level indicator 16, 17 and 18 is mounted and wired, or operates, is optional. Finally, the lid 25 (FIG. 2) by means of which the covering of the substitution chamber formed in the receptacle 1 or 1a is possible, can have a screw or bayonet lock, and the form and make of the dewar flask 4 and of the linking elements which are provided between the dewar flask 4 and the receptacle 1 or 1a are optional.

What is claimed is:

1. A device for the cryosubstitution of small biological specimens for microscopic, especially electron microscopic investigations, which comprises a metal receptacle for receiving at least one specimen, a dewar flask for holding a liquid cryogen, mounting means to support said receptacle in said dewar flask above the level of the cryogen, means to regulate the temperature of said receptacle by the cryogen and a heating device, a radiation shield mounted between the underside of the receptacle and the cryogen to reduce the heat radiation from the receptacle into the into the cryogen, said receptacle being adapted to contain a substitution medium covering the specimens, whereby the specimen and substitution medium can be held at a temperature between $-30°$ C. and $-120°$ C. by a cold circulating atmosphere.

2. The device, according to claim 1, wherein said receptacle has at least one groove to achieve a specific heat exchange with the gas atmosphere.

3. The device, according to claim 2, wherein the groove is helical.

4. The device, according to claim 1, further including means for providing temporary circulation of cryogen gas to increase the rate of heat exchange.

5. The device, according to claim 1, further including a heat-conducting metal connection having a preselected thermal resistance contacting said receptacle and liquid cryogen.

6. The device, according to claim 5, further including adjustment means to provide selection of the penetration of said metal connection into the cryogen and the duration of contact with both said receptacle and cryogen.

7. The device, according to claim 6, wherein said receptacle includes heating means.

8. The device, according to claim 7, wherein said heating means is activated by a semi or fully automatic control for time-dependent control of the temperature curve.

9. The device, according to claim 8, further including means to adjust the temperature curve.

* * * * *